US012642521B2

(12) United States Patent
Brady et al.

(10) Patent No.: US 12,642,521 B2
(45) Date of Patent: Jun. 2, 2026

(54) METHODS OF TISSUE REPAIRS

(71) Applicant: ARTHREX, INC., Naples, FL (US)

(72) Inventors: Paul C. Brady, Knoxville, TN (US);
Andrew C. Petry, Naples, FL (US);
Shaun G. Leblanc, Naples, FL (US);
Jennifer Brooks, Naples, FL (US)

(73) Assignee: Arthrex, Inc., Naples, FL (US)

( * ) Notice: Subject to any disclaimer, the term of this
patent is extended or adjusted under 35
U.S.C. 154(b) by 279 days.

(21) Appl. No.: 18/301,551

(22) Filed: Apr. 17, 2023

(65) Prior Publication Data

US 2024/0341750 A1     Oct. 17, 2024

(51) Int. Cl.
A61B 17/04          (2006.01)

(52) U.S. Cl.
CPC ...... *A61B 17/0469* (2013.01); *A61B 17/0491*
(2013.01); *A61B 2017/0409* (2013.01); *A61B*
*2017/0464* (2013.01); *A61B 2017/0496*
(2013.01)

(58) Field of Classification Search
CPC ............ A61B 17/0469; A61B 17/0491; A61B
2017/0409; A61B 2017/0464; A61B
2017/0496
See application file for complete search history.

(56) References Cited

U.S. PATENT DOCUMENTS

| | | | |
|---|---|---|---|
| 1,822,330 A | 9/1931 | Ainslie | |
| 5,312,423 A | 5/1994 | Rosenbluth et al. | |

| | | | |
|---|---|---|---|
| 5,643,293 A | 7/1997 | Kogasaka et al. | |
| 5,895,393 A | 4/1999 | Pagedas | |
| 5,895,395 A | 4/1999 | Yeung | |
| 8,177,795 B2 | 5/2012 | Niese et al. | |
| 9,358,001 B2 | 6/2016 | Fan et al. | |
| 10,004,489 B2 * | 6/2018 | Kaiser .............. | A61B 17/06166 |
| 10,022,122 B2 | 7/2018 | Singhatat et al. | |
| 11,013,510 B2 | 5/2021 | Saliman et al. | |
| 11,389,156 B2 | 7/2022 | Harrison et al. | |
| 12,082,801 B2 * | 9/2024 | Dooney, Jr. ........... | A61F 2/0811 |

(Continued)

FOREIGN PATENT DOCUMENTS

| | | | |
|---|---|---|---|
| EP | 1306056 B1 | 5/2003 | |
| EP | 2042104 A1 | 4/2009 | |

(Continued)

OTHER PUBLICATIONS

International Search Report and Written Opinion for International
Application No. PCT/US2024/023656 dated Sep. 27, 2024.

(Continued)

*Primary Examiner* — Phong Son H Dang
(74) *Attorney, Agent, or Firm* — Potomac Law Group,
PLLC

(57)          ABSTRACT

Methods for tissue repairs with mattress stitch are disclosed.
A mattress stitch is created with a suturing construct that
includes one or more soft-body anchors and a flexible strand
attached to the soft-body anchors. A free, tensionable end of
the flexible strand is removably attached to a suture passer
and passed through the tissue. The free end is then passed
through the soft-body anchors to form a knotless, continu-
ous, uninterrupted, flexible, adjustable, self-locking, ten-
sionable loop around and through the tissue.

16 Claims, 6 Drawing Sheets

(56) References Cited

U.S. PATENT DOCUMENTS

| | | | | |
|---|---|---|---|---|
| 12,096,928 | B2* | 9/2024 | Kaiser | A61B 17/0487 |
| 2002/0103493 | A1 | 8/2002 | Thal | |
| 2003/0078599 | A1 | 4/2003 | O'Quinn et al. | |
| 2004/0260314 | A1 | 12/2004 | Lizardi et al. | |
| 2007/0225735 | A1 | 9/2007 | Stone et al. | |
| 2007/0276395 | A1 | 11/2007 | Burn | |
| 2008/0027468 | A1 | 1/2008 | Fenton et al. | |
| 2008/0154286 | A1 | 6/2008 | Abbott et al. | |
| 2008/0208221 | A1 | 8/2008 | Murray et al. | |
| 2009/0088781 | A1 | 4/2009 | Prestel et al. | |
| 2009/0228041 | A1 | 9/2009 | Domingo | |
| 2010/0106169 | A1 | 4/2010 | Niese et al. | |
| 2010/0305581 | A1 | 12/2010 | Hart | |
| 2012/0283753 | A1 | 11/2012 | Saliman et al. | |
| 2012/0283754 | A1 | 11/2012 | Murillo et al. | |
| 2013/0158567 | A1 | 6/2013 | Levin et al. | |
| 2014/0052178 | A1* | 2/2014 | Dooney, Jr. | A61B 17/0401 606/232 |
| 2014/0249577 | A1* | 9/2014 | Pilgeram | A61B 17/0485 606/228 |
| 2014/0277133 | A1* | 9/2014 | Foerster | A61B 17/0401 606/232 |
| 2015/0173739 | A1 | 6/2015 | Rodriguez et al. | |
| 2015/0173742 | A1 | 6/2015 | Palese et al. | |
| 2016/0157904 | A1 | 6/2016 | Zeetser et al. | |
| 2017/0049432 | A1* | 2/2017 | Dooney, Jr. | A61B 17/0487 |
| 2017/0112492 | A1 | 4/2017 | Juan et al. | |
| 2018/0125472 | A1 | 5/2018 | Dreyfuss | |
| 2019/0247039 | A1 | 8/2019 | Gregoire et al. | |
| 2020/0054439 | A1 | 2/2020 | Holowecky et al. | |
| 2020/0138429 | A1 | 5/2020 | Dreyfuss et al. | |
| 2020/0275922 | A1 | 9/2020 | Valentin et al. | |
| 2021/0236115 | A1 | 8/2021 | Radfar et al. | |
| 2021/0275165 | A1 | 9/2021 | Rash | |

FOREIGN PATENT DOCUMENTS

| | | |
|---|---|---|
| WO | 2009111591 A2 | 9/2009 |
| WO | 2013093620 A2 | 6/2013 |

OTHER PUBLICATIONS

Invitation to pay Additional Fees for International Application No. PCT/US2024/023656 dated Jul. 15, 2024.

International Search Report and Written Opinion for International Application No. PCT/US2023/082661 dated Jun. 28, 2024.

Invitation to Pay Additional Fees For International Application No. PCT/US2023/082661 dated Apr. 15, 2023.

Unknown. "The Cross Fix II System," Zimmer Biomet, health care professional material, 2018.

Extended European Search Report issued in EP Pat. Appln. No. 23913433.1 and dated Mar. 19, 2026.

* cited by examiner

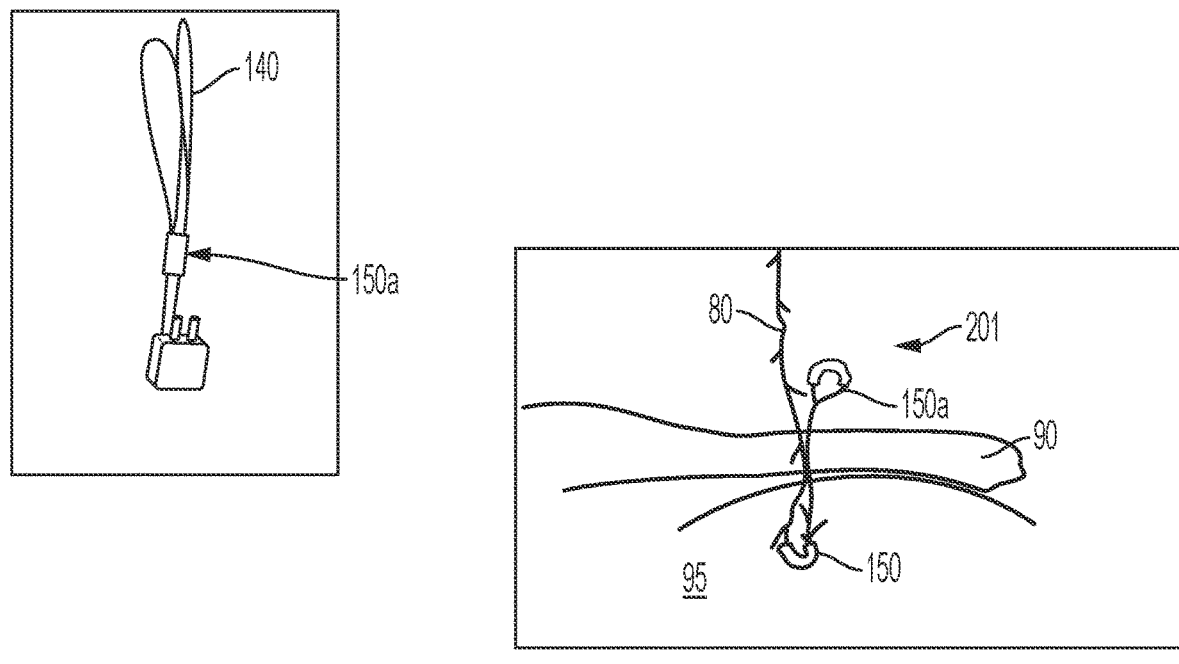
FIG. 14
FIG. 15
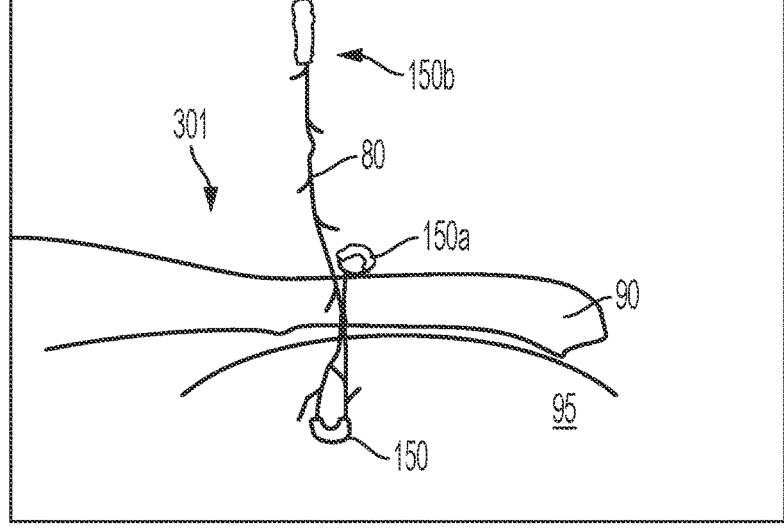
FIG. 16

METHODS OF TISSUE REPAIRS

BACKGROUND

The disclosure relates to the field of surgery and, more specifically, to methods of passing suture for tissue repairs.

SUMMARY

A surgical construct is disclosed. A first tissue is attached to a second tissue with a surgical construct that includes one or more self-locking anchors on one side of the construct and a horizontal mattress suture on another side of the construct. The surgical construct can be knotless, adjustable, tensionable and self-locking.

Methods for surgical repairs are disclosed. A first tissue is attached to a second tissue while maintaining anchors outside a joint space, without deploying anchors within the joint space. A first tissue can be a graft and a second tissue can be soft tissue such as rotator cuff. By placing the anchors outside the joint space, a graft can be secured in a quick, easy, and safe manner.

A suture passer of a suture passer/anchor assembly can penetrate tissue at two different points and blindly pass and retrieve suture through an area of the tissue. Once the suture has been passed through the tissue and the suture passer has been pulled out of the tissue, the suture is passed through an anchor of the suture passer/anchor assembly maintained outside the joint space. The anchor is slid down towards the tissue until the anchor rests upon the tissue and is tensioned to form a cinch stitch. The suture can be subsequently passed through additional anchors. At least one of the anchors can be a soft anchor. At least one of the anchors can be a soft anchor with a locking structure such as a barbed suture that prevents the construct from loosening and provides a knotless, adjustable, tensionable, self-locking repair.

Methods of forming a knotless, self-locking mattress suture with an anchor assembly are also disclosed. The anchor assembly can include one or more anchors. At least one of the anchors can be a soft anchor.

A soft anchor is pre-loaded with a flexible strand. A first portion of the flexible strand (suturing and tensioning end) can be passed blindly through tissue with a suture passer. A first portion of a flexible strand can be blindly passed horizontally underneath tissue. A suture passer can pierce through tissue at desired locations of entry and exit of the flexible strand. A needle can pass from one tooth to the other, passing the first portion of a flexible strand from one tooth to the other tooth and up through the tissue. Once the flexible strand has been passed through and pulled out of the tissue, the first portion of the flexible strand is passed through the soft anchor. The anchor is slid down toward the tissue until the anchor rests upon the tissue and forms a cinch stitch. The steps can be repeated for multiple soft anchors to form mattress stitches.

At least one of the multiple anchors can be a soft anchor. At least one of the multiple anchors can be a soft anchor with a locking structure in the form of a second portion of the flexible strand. The locking structure can be one or more barbs or spiks that prevent the construct from loosening, providing a knotless, adjustable, self-locking tissue repair. A barbed suture can terminate in the first portion of the flexible strand.

Methods of adding an additional anchor or anchors that can be deployed above or below the tissues to create a running stitch are also disclosed. A soft anchor can be added on to the flexible strand after the first pass of the tissue. The end of the flexible strand could then be passed again, creating another stitch. The steps can be repeated as many times as desired.

BRIEF DESCRIPTION OF THE DRAWINGS

FIG. 14 illustrates another view of a suture passer and fixation device.

FIGS. 15 and 16 illustrate schematic subsequent steps of another tissue repair.

DETAILED DESCRIPTION

Figure 1:
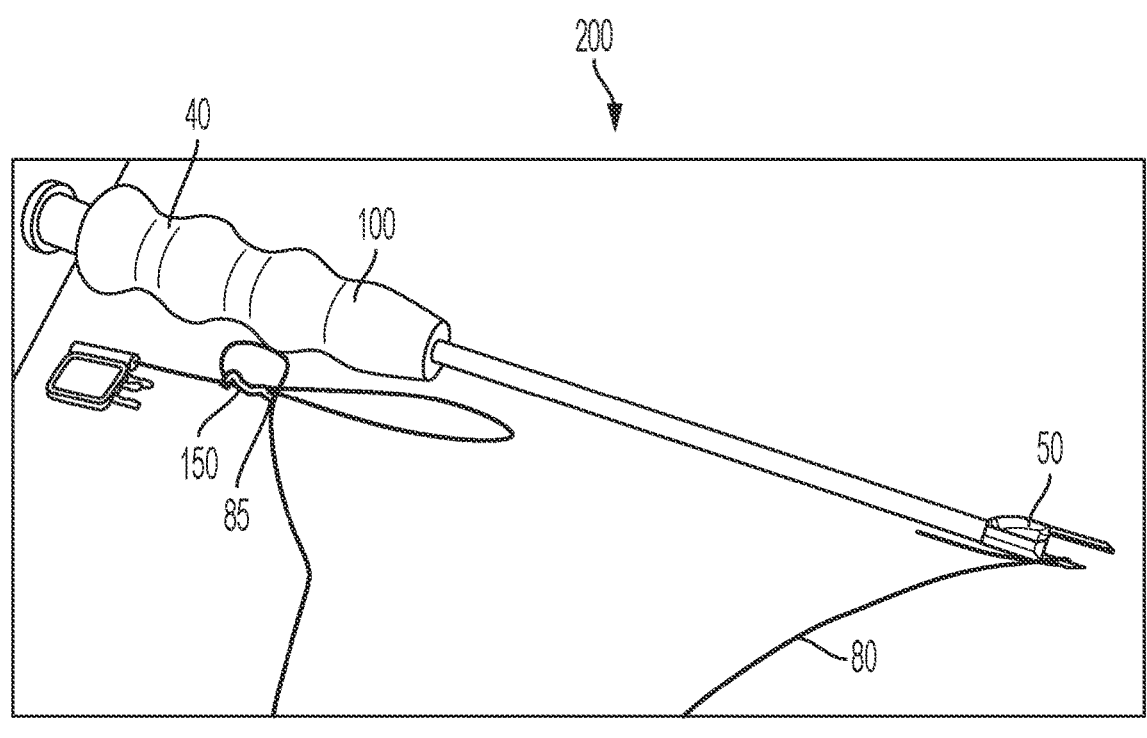
FIG. 1 illustrates a surgical assembly with a suture passing instrument and fixation device.

The disclosure provides surgical systems, assemblies, constructs, and methods for tissue repairs and reconstructions.

A surgical assembly includes one or more knotless fixation devices preloaded with a flexible strand and a suture passer. One portion or one end (a first portion or first end; a suturing end; a tensioning end) of the flexible strand is secured to the suture passing instrument. Another portion or another end (a second portion or second end) of the flexible strand is fixedly attached to a fixation device. The second end can include a locking structure or locking mechanism in the form of a barbed or spiked suture. The fixation device is maintained outside the joint space. The suture passer can be provided with means to penetrate two distinct points in a tissue and blindly pass and retrieve the first portion of the flexible strand through an area of the tissue. Means can include sharp teeth and/or pointed structures such as tines. After passing through the tissue, the first portion of the flexible strand can be passed through the fixation device to form a knotless, continuous, uninterrupted, flexible, adjustable, self-locking, tensionable loop around and through the tissue. The fixation device can be secured against the tissue by pulling on the flexible strand. The second end of the flexible strand can include a one-way locking structure/ mechanism that locks the repair and prevents the construct from loosening. The steps can be repeated for additional fixation devices. At least one of the fixation devices can be a soft anchor such as a soft-body anchor consisting essentially of suture. The repair is a self-locking, knotless, tensionable repair with one or more fixation devices on top and a horizontal suture mattress on bottom. The repair does not require deployment of the fixation devices within the joint space.

Methods of knotless, self-locking, tensionable tissue repairs are also disclosed. A first tissue is attached to a second tissue while maintaining anchors outside a joint space, without deploying anchors within the joint space. A first tissue can be a graft and a second tissue can be soft tissue such as rotator cuff. By placing the anchors outside the joint space, a graft can be secured in a quick, easy, and safe manner. A first end (first region; flexible end; suturing end; tensioning end; free end) of a flexible construct is passed through two separate points or locations in tissue (soft tissue, or graft and soft tissue) with a suture passer, the suture passer is removed, and the first end is passed through a tubular sheath of a soft anchor maintained outside the joint space. The soft anchor is slid towards the tissue to secure the soft anchor over the tissue. The flexible construct has a second end (second region; fixed end; opposite end) which can be fixedly attached to the anchor by a knot or loop or similar structure. The second end can include a region with a self-locking structure or mechanism, for example, one or more uni-directions barbs or spikes. The locking structure can be a barbed or spiked suture, or barbed or spiked filament, or suture or filament provided with indentations/protuberances/bumps/protrusions or combinations thereof. The second end can be adjacent to and contiguous with the first end. The method provides a means to attach a graft material to tissue such as rotator cuff while keeping anchors outside the joint space. Multiple anchors (fixation devices) can be employed for the repair. The steps can be repeated for each additional anchor (fixation device).

Referring now to the drawings, where like elements are designated by like reference numerals, FIGS. 1-16 illustrate exemplary surgical repairs 101, 201, 301 (Fiber Zip repairs) of the present disclosure.

FIGS. 1-13 illustrate an exemplary surgical assembly 200 (surgical system 200) that includes suture passing instrument 100, fixation device 150, and flexible construct 80 employed in an exemplary method of tissue repair 101 (shoulder repair 101) of the present disclosure. Although, for ease of understanding, tissue repair 101 will be described below with reference to only one fixation device 150, it must be understood that the disclosure is not limited to this exemplary-only embodiment. Accordingly, the disclosure also contemplates surgical tissue repairs wherein any number of additional fixation devices can be employed, as required by the specific repairs and as desired by the surgeon. In certain embodiments, any or all additional fixation devices can be additional soft anchors (soft suture anchors; all-suture soft anchors) in the form of self-locking, tensionable, knotless anchors.

Suture passing instrument 100 (suture passer 100; instrument 100; surgical instrument 100) can be any suture passer known in the art, for example, Arthrex SwiftStitch™ suture passer, Arthrex Scorpion™ suture passer, Arthrex SutureLasso suture passer, Arthrex Rotation Lasso suture passer, Arthrex BirdBeak® suture passer, Arthrex Penetrator™ retriever, etc. Thus, although the embodiments detailed below will be explained with reference to a particular and exemplary-only suture passer, the disclosure is not limited to this exemplary-only suture passer and contemplates the use of any suture passer known in the art.

Exemplary-only suture passer 100 shown in FIGS. 1-7 comprises an elongated tubular member or shaft 12 with a longitudinal axis, a proximal end 11, a distal end 13 and an axial throughbore therein. Details of exemplary-only suture passer 100 are set forth in U.S. application Ser. No. 18/090,593, entitled "SUTURE PASSER AND METHODS OF TISSUE REPAIR" filed on Dec. 29, 2022, the disclosure of which is incorporated in its entirety herein.

As detailed in U.S. application Ser. No. 18/090,593, elongated tubular member 12 connects, and extends between, a handle assembly 40 and a tip 50 designed to pierce tissue. Tip 50 (illustrated enlarged in FIGS. 2, 3 and 7) is provided with first and second teeth 60, 70 (first and second jaws 60, 70; lower and upper jaws 60, 70; tines 60, 70; first and second jaw members 60; 70) provided integral with shaft 12. First tooth 60 is provided with a sharp distal point 61, a passage (not shown) for receiving a needle 30, and a distal opening 65 to allow the needle to pass through.

Opening 65 also allows a first portion of flexible construct 80 (flexible strand 80) to pass and extend therethrough, as detailed below. Opening 65 is provided in a most distal end of tip 50 and communicates with the needle passage. Distal opening 65 allows suture 80 to exit in a direction non-parallel to the longitudinal axis of the instrument.

Second tooth 70 is also provided with a sharp distal point 71, and a distal opening 75 to allow the needle 30 and flexible construct 80 to pass through. Opening 75 can be a through opening that allows a first portion of flexible construct 80 to pass and extend therethrough, as detailed below. Second tooth 70 also comprises a securing mechanism 77 (illustrated in more detail in FIG. 7) located in about same plane as the distal opening 75, to allow the first portion 81 of flexible construct 80 to be secured thereto when the device 100 is pulled out of the tissue. First and second teeth 60, 70 have different lengths.

Flexible construct 80 (flexible strand 80; suture 80; suture strand 80; suturing construct 80; flexible construct 80; flexible material 80; barbed suture 80) is provided with a first portion 81 (first end 81; tail 81; flexible end 81; suturing end; tensioning end 81) terminating with a second portion 85 (second end 85; fixed end 85; opposite end 85). First end 81 can be stiffened to allow convenient and easy advancement through the tissue and openings 65, 75 of the suture passer 100. The second end 85 can include suture or filament provided with a locking structure or mechanism, such as barbs, disposed on the second end. The locking structure can include a plurality of indentations/protuberances/bumps/protrusions/barbs/spikes or combinations thereof. The second end 85 can be barbed or spiked suture. The second end 85 provides a locking mechanism to the construct. As shown in FIG. 1, first end 81 of flexible construct 80 is removably attached to the lower tooth 60 of suture passer 100. Second end 85 of flexible construct 80 is fixedly attached to the fixation device 150 by a knot or a loop, such as loop 88 (FIGS. 12 and 13).

Figure 12:
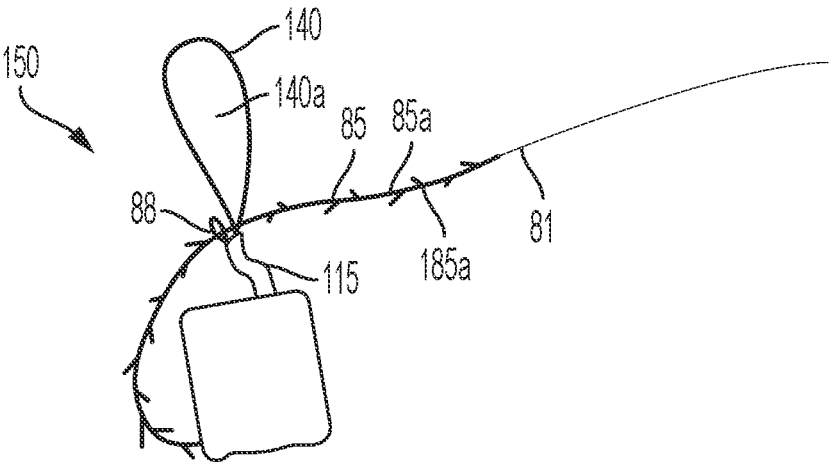
FIG. 12 is an enlarged view of the fixation device of the surgical assembly of FIG. 1 (with an attached shuttle/pull device).
Figure 13:
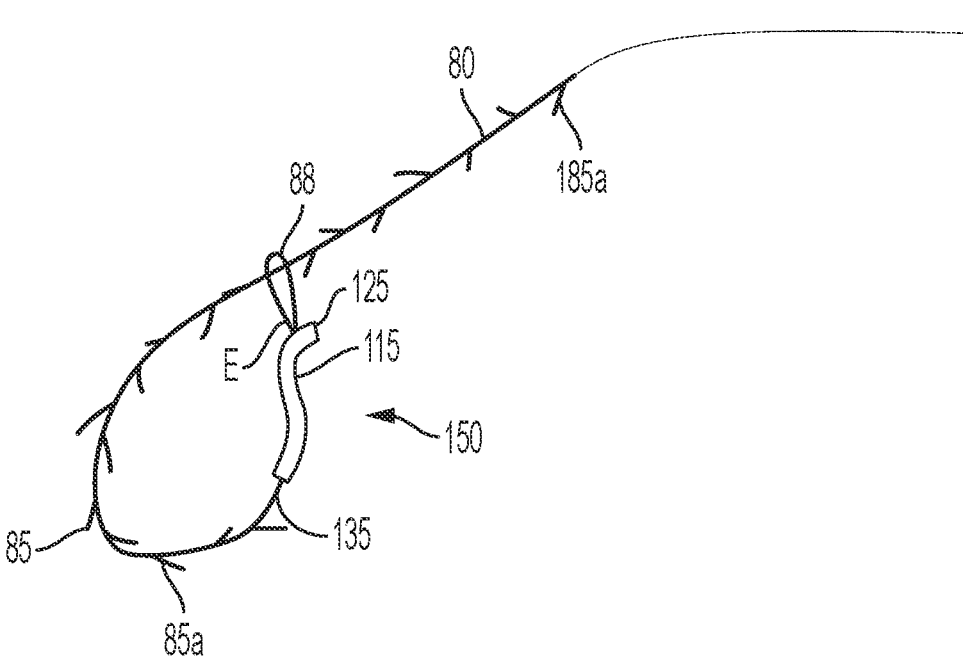
FIG. 13 is an enlarged view of the fixation device of the surgical assembly of FIG. 1 (without a shuttle/pull device).

Fixation device 150 of exemplary assembly 200 of FIG. 1 is shown in more detail in FIGS. 12 and 13. In an embodiment, fixation device 150 is a self-locking, tensionable, knotless anchor. In an embodiment, fixation device 150 is in the form of a soft anchor (soft suture anchor, or all-suture soft knotless anchor, or soft body suture anchor) provided with a soft anchor sleeve 115 (sheath or tubular member 115) with two open ends 125, 135. Flexible coupler 80 extends through the soft anchor sleeve (sheath). One of more shuttle/pull devices 140 (FIG. 12) can also extend through the sleeve, in similar or different directions and/or orientations and/or locations.

The flexible coupler 80 can be passed through at least a portion of the body of the fixation device 150, for example, through a full cannulation of the fixation device (from one open end 125, 135 to the other open end 125, 135), or can exit the body of the fixation device at a location other than most distal end and most proximal end of the fixation device. FIG. 13 illustrates flexible coupler exiting the sheath 115 at a location E which is spaced from the opening end 125 of the sheath 115, and forming a fixed loop 88.

As shown in FIGS. 12 and 13, second end 85 (fixed end 85) of flexible coupler 80 can include a locking structure 85a disposed on the flexible coupler. The locking structure can consist of at least one spike or barb 185a to provide a one-way locking mechanism of the final repair. Locking structure 85a is provided on the flexible coupler to prevent loosening of the suture construct once graft is secured against the tissue. Locking structure 85a can be configured to provide a one-way lock. The one-way lock can be created, for example, using one or more uni-directional barbs 185a.

As illustrated in FIGS. 12 and 13, the barbs can preferably angle outwardly in a direction toward soft anchor 150. The one or more barbs 185a can be provided on a portion of flexible construct 80, preferably a portion of the construct that is closer to the sheath 115 of soft anchor 150 than the tensioning free end 81. Alternatively, barbs 185a can be provided continuously or discontinuously along the length of flexible construct 80. Barbs or spikes 185a can also extend from one or more sides or areas of flexible construct 80. In an embodiment, the barbs 185a are overmolded onto end 85 of flexible construct 80.

Details of an exemplary soft suture anchor with a soft anchor sleeve (sheath or tubular member) and flexible shuttling strands as well as barbed suture strands are set forth, for example, in U.S. Pat. No. 10,849,734 entitled "Methods of Tissue Repairs" issued on Dec. 1, 2020, and U.S. Pat. No. 10,524,776 entitled "Soft Suture Anchor Assembly with Barbed Suture and Attached Tissue Fixation Disk" issued on Jan. 7, 2020, the disclosures of both of which are incorporated by reference in their entireties herein. The flexible coupler and the shuttle/pull device(s) can extend through the sleeve in similar or different directions and/or orientations and/or locations.

As detailed below, free end 81 of flexible coupler 80 is passed through the tissue 90 and then through an eyelet/loop 140a of suture passing device 140. Suture passing device 140 is then pulled, thereby pulling free end 81 of the flexible coupler 80 towards the body of the fixation device 150, inside of the sheath 115 and then exiting the sheath 115 to form a flexible, closed, knotless, continuous, self-locking, cinching loop 188 around and through tissue 90. These steps can be repeated for the formation of additional loops with the aid of additional suture passing devices 140 and/or additional fixation devices. Free end 81 of the flexible coupler 80 can be pulled to shrink and tension the construct and the flexible, closed, knotless, self-locking, continuous, adjustable, cinching loop 188, providing a final repair/construct 101 with increased compression of tissue.

Reference is now made to FIGS. 2-10 which illustrate schematic steps of a method of tissue repair (e.g., tendon or ligament repair) with suture passer/fixation device assembly 200 including exemplary instrument 100 and fixation device 150 loaded with exemplary flexible strand 80. One end of flexible strand 80, for example, fixed end 85, is securely attached to fixation device 150 by providing fixed loop 88 spaced apart from the most distal end 125 and at location E (FIG. 13). At least a portion of flexible strand 80 can be provided with a locking mechanism 85a (for example, a plurality of spikes or barbs 85a provided along a length of flexible strand 85). The opposite end of flexible strand 80, for example, free end 81, is loaded onto instrument 100, as shown in FIG. 1. Free end 81 can be removably loaded onto the lower jaw 60 (short tine 60) of suture passer 100.

Figure 2:
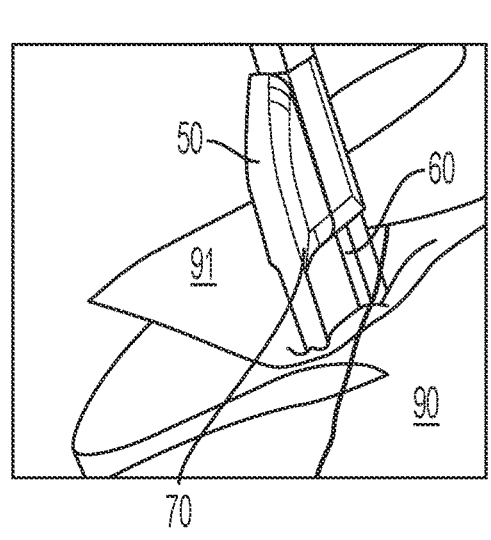
FIGS. 2-11 illustrate schematic subsequent steps of a tissue repair with the suture passing instrument and fixation device of FIG. 1.
Figure 3:
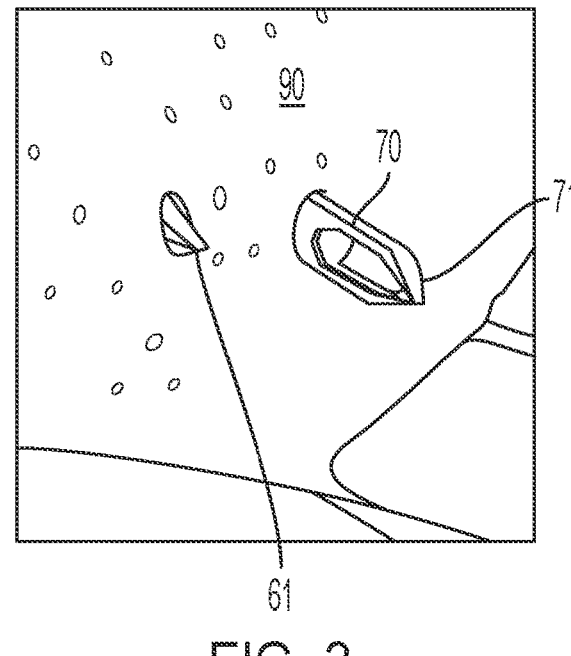

FIGS. 2 and 3: Suture 81 is loaded onto short tine 60 of the device 100. The distal end of the device 100 is inserted through a cannula and into tissue 90, or into tissue 90 and graft 91 (FIG. 2). Instrument 100 loaded with flexible strand 80 is passed through tissue 90 or through tissue 90 and associated graft 91; instrument 100 pokes tissue 90 (or tissue 90 and graft 91), for example, pierces tissue 90 (or tissue 90 and graft 91) at two different locations A, B. Alternatively, instrument 100 can pass under the tissue 90 (e.g., tendon).

Figure 4:
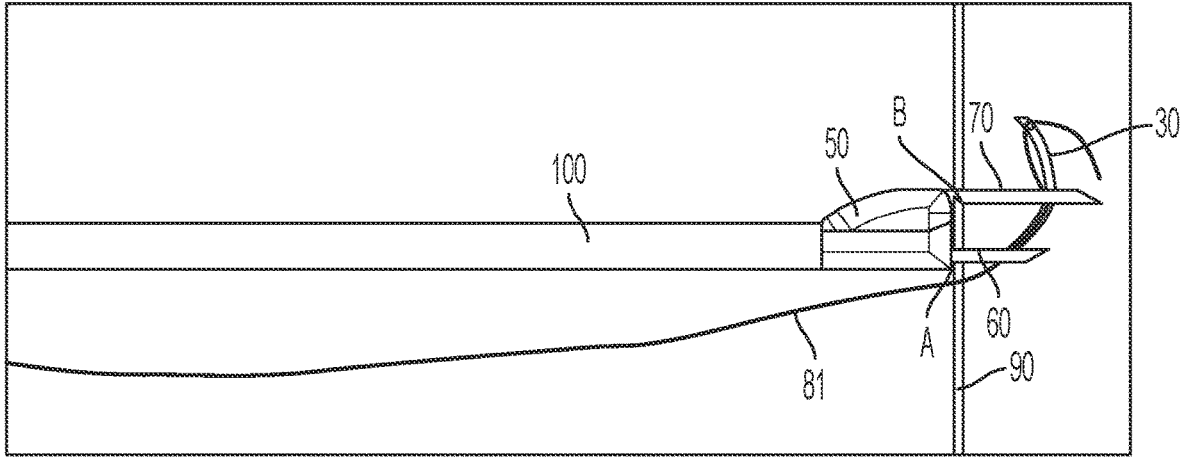

FIG. 4: Once the appropriate depth is attained in tissue 90 (or tissue 90 and graft 91), needle 30 is fired, transferring suture 81 through the window 75 of the longer tine 70.

Figure 5:
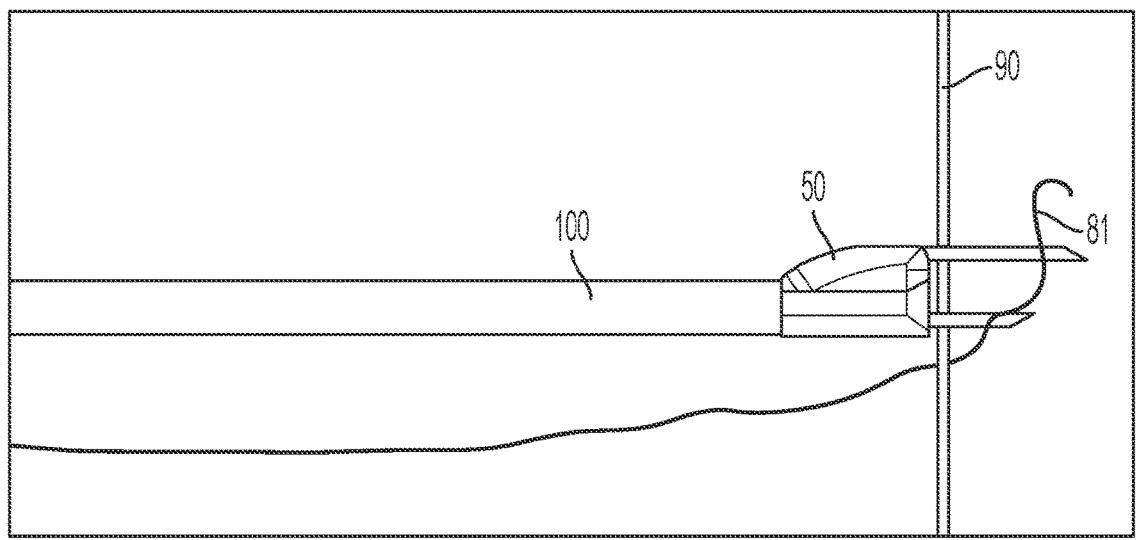

FIG. 5: The needle 30 is retracted back into the short tine 60 leaving the suture 81 in the longer tine window 75.

Figure 6:
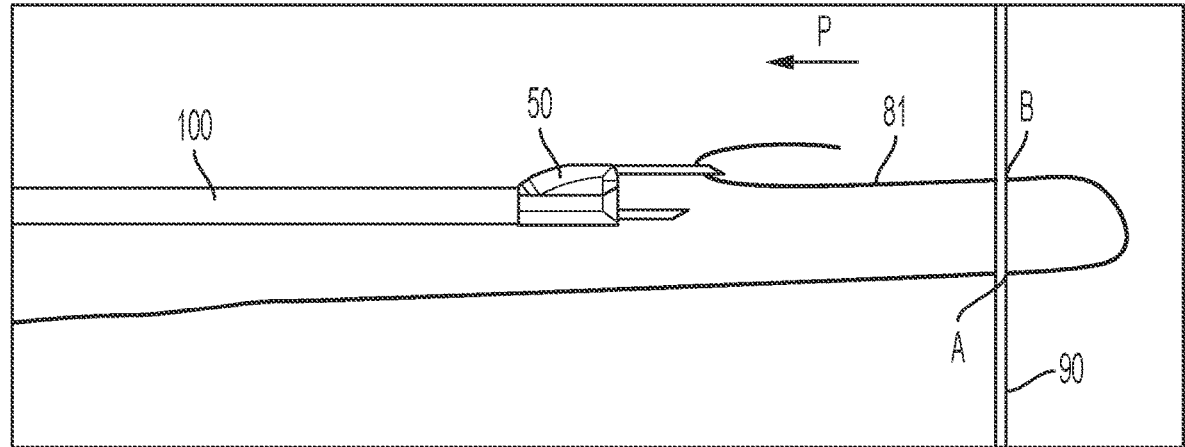
Figure 7:
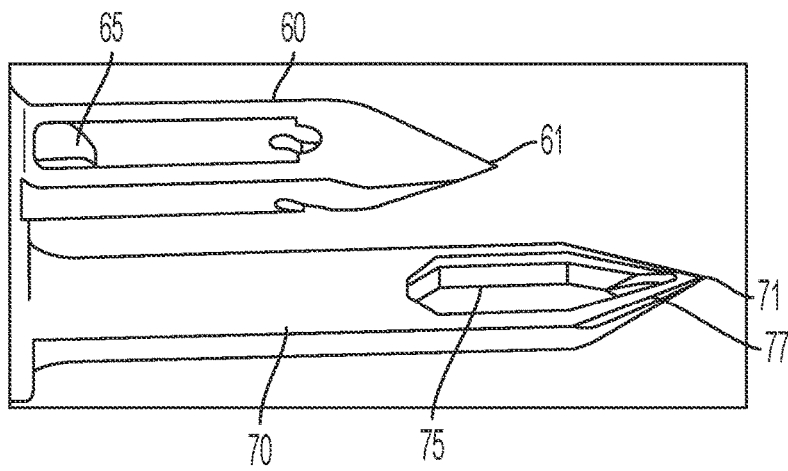

FIG. 6: The device 100 is pulled out of the tissue 90 (or tissue 90 and graft 91) in the direction of arrow P. The suture 81 folds over the distal wall of the longer tine window 75 and catches on a suture catch spike 77 (securing mechanism 77). FIG. 7 illustrates an enlarged view of the suture securing mechanism 77 of the upper tooth 70. Device 100 can be removed, and the free end 81 of suture 80 is released from the longer tine 70.

Figure 8:
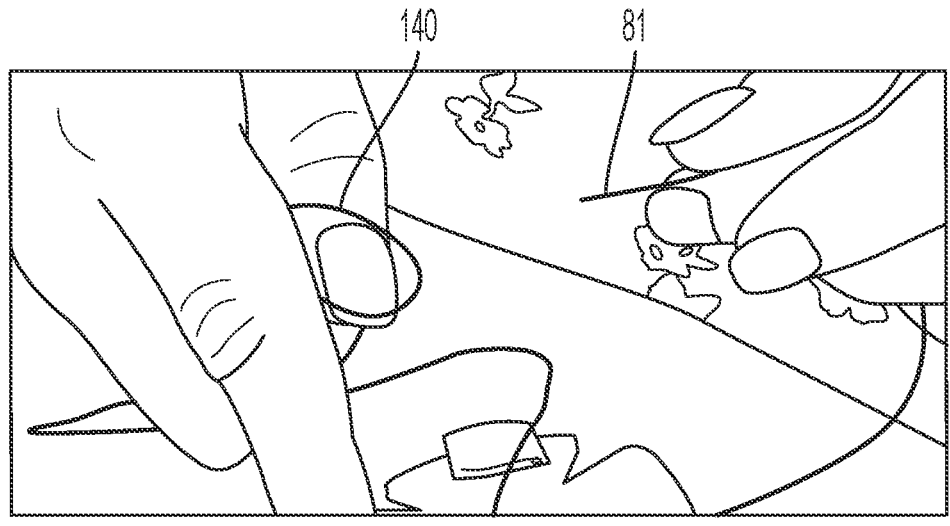

FIG. 8: Thread the free end 81 of the suture through the suture flag 140 (through loop 140a of shuttle/pull device 140) and pull through the soft-body anchor 150. Pull to start sliding the anchor 150 towards the tissue 90.

Figure 9:
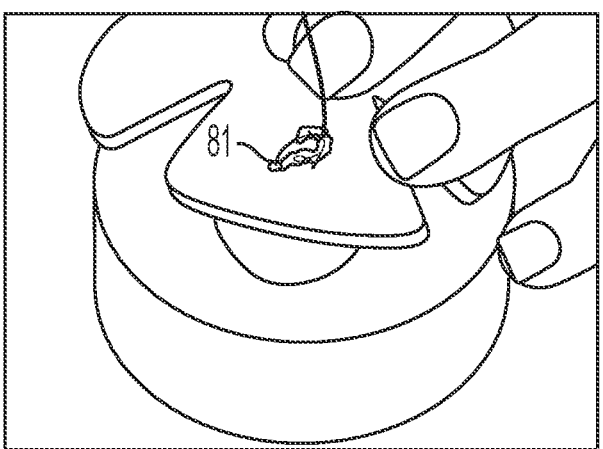

FIG. 9: Continue to pull the suture 81 through until the soft-body anchor 150 is snug against the graft 91 and/or tissue 90. The barbed suture 85a pulls one way though the soft-body anchor 150, preventing the construct from loosening.

Figure 10:
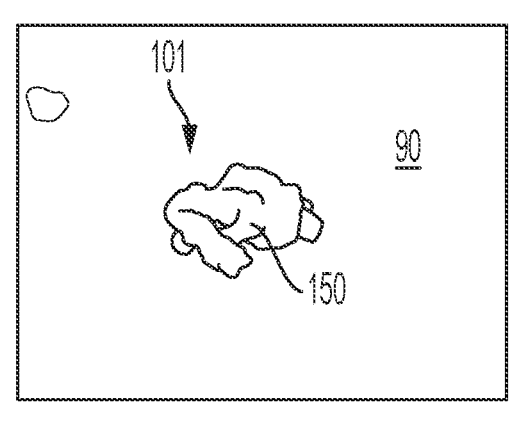
Figure 11:
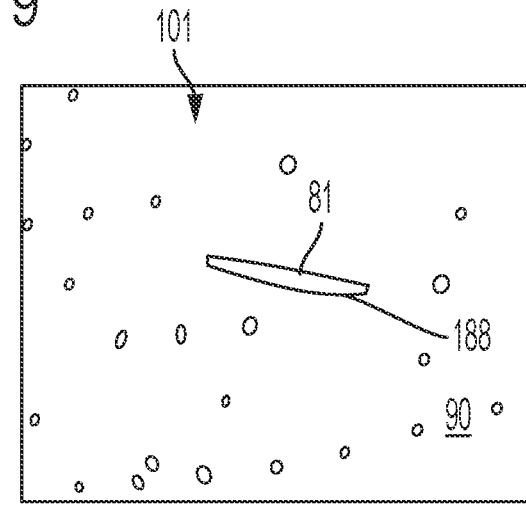

FIGS. 10 and 11: Trim any excess suture 80. The final construct 101 leaves a self-locking anchor 150 on top (FIG. 10) with a horizontal mattress suture 188 (a flexible, closed, knotless, self-locking, continuous, adjustable, cinching loop 188) on bottom (FIG. 11).

Flexible strand 80 can be formed of a single strand of material that is securely and fixedly attached to fixation device 150 by a loop or a knot or a similar structure. In one embodiment, the perimeter of loop 88 can be fixed. Loop 88 may be formed by splicing the flexible strand through itself, or by other methods known in the art, such as fusion, gluing, bonding, joining, braiding, interlinking, etc. In one embodiment, regions/ends 85 and 81 of flexible strand 80 can be formed of suture having a round cross-section. The suture can have the same or different diameters. In one embodiment, flexible strand 80 can be securely and fixedly attached to fixation device 150 by a knot, for example, a static knot.

In additional embodiments, the disclosure provides methods of adding an additional anchor or adding additional multiple anchors that can be deployed above or below the tissues to create a running stitch. One or more soft anchors could be added on to the flexible strand after the first pass of the tissue. The end of the flexible strand could then be passed again, creating another stitch. The process can be repeated as many times as desired, and for as many anchors as necessary.

For example, and referring to FIG. 14, subsequent to the repair with soft anchor 150, another soft anchor 150a can be loaded or pre-loaded onto nitinol suture passer 140. Free end 81 of flexible strand 80 can be passed through the loop 140a so that, pulling the tab will pull the flexible strand 80 through the soft anchor 150a to reinforce the repair and create additional suture passes/tensionable, knotless loops. The steps can be repeated with and for multiple soft anchors and/or additional fixation devices, as desired and as required by the specific soft tissue repair.

FIGS. 15 and 16 illustrate subsequent steps of a method of tissue repair 301 with multiple anchors. A third anchor, for example, a third soft anchor 150b is added to the flexible strand 80 subsequent to repair 201 of FIG. 15. First tissue 90 (for example, soft tissue) can be attached to second tissue 95 (for example, bone) by employing one or more soft anchors (for example, soft anchors 150, 150a, 150b). The plurality of anchors can all reside on top of the repaired tissue 90. In other embodiments, and as shown in FIG. 16, one or more anchors can reside within the second tissue 95, whereas the other anchors can reside on top of the first tissue 90. Multiple anchors can be employed for the repair. In an embodiment, all the multiple anchors are soft tissue anchors. Repair 301 can be an exemplary rotator cuff repair.

Flexible strand 80 can include a single filament, or fiber, or can include multiple continuous filaments, segments or regions of filaments that have different configurations (for example, different diameters and/or different compositions). The filament regions/segments may each be homogenous (i.e., formed of a same material) or may be a combination of homogenous and heterogenous (i.e., formed of a plurality of materials). Exemplary materials may include suture, silk, cotton, nylon, polypropylene, polyethylene, ultrahigh molecular weight polyethylene (UHMWPE), polyethylene terephthalate (PET), and polyesters and copolymers thereof, or combinations thereof.

In an embodiment, the flexible strand 80 is made of any known suture construct, such as multifilament, braided, knitted, woven suture, or including fibers of ultrahigh molecular weight polyethylene (UHMWPE) or the Fiber-Wire® suture (disclosed in U.S. Pat. No. 6,716,234, the disclosure of which is hereby incorporated by reference in its entirety herein). The flexible strand 80 can be also formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein. Flexible strand 80 can also include, and be manufactured with, any kind of material (suture, nylon, silk, UHMWPE, metal, bioabsorbable, etc.) that can allow the flexible strand to form a loop terminating in a free end.

Flexible strand 80 can be coated (partially or totally) with wax (beeswax, petroleum wax, polyethylene wax, or others), silicone (Dow Corning silicone fluid 202A or others), silicone rubbers (Nusil Med 2245. Nusil Med 2174 with a bonding catalyst, or others) PTFE (Teflon, Hostaflon, or others), PBA (polybutylate acid), ethyl cellulose (Filodel) or other coatings, to improve lubricity of the suture. loop security, pliability, handleability or abrasion resistance, for example. Flexible strand 80 can be also provided with tinted tracing strands. or otherwise contrast visually with other areas/regions of the construct, which remains a plain, solid color, or displays a different tracing pattern, for example. Various structural elements of flexible strand 80 such as ends 81, 85 may be visually coded, making identification and handling of the suture loops and ends simpler. Easy identification of suture in situ is advantageous in surgical procedures.

Methods of soft tissue repair which do not require tying of knots and allow tissue suturing and/or graft attachment to tissue while keeping fixation devices outside the joint space are disclosed. A method of knotless, self-locking tissue repair comprises inter alia the steps of: (i) loading a flexible coupler 80 on a fixation device 150 provided with at least one shuttle/pull device 140 by passing the flexible coupler 80 through a body 115 of the fixation device 150 and fixedly attaching the flexible coupler 80 to the fixation device 150; (ii) loading a free end 81 of the flexible coupler onto a suture passer 100; (iii) with the fixation device 150 maintained outside the joint space, piercing tissue 90 with the suture passer 100 and passing the flexible coupler 80 through the tissue 90; (iv) pulling the suture passer 100 and the flexible coupler 80 out of the tissue 90; and (v) passing the free end 81 through loop/eyelet 140*a* of shuttle/pull device 140 to pull the free end 81 through body 115 of suture anchor 150 to form a flexible, closed, knotless, self-locking, continuous, adjustable, cinching loop 188 around and through the tissue 90 (a suture mattress stitch) of repair 101.

An exemplary method of suturing tissue comprises: (i) fixedly attaching a first end 85 of a flexible construct 80 to a soft anchor 150, and removably attaching a free end 81 of the flexible construct 80 to a suture passer 100; (ii) piercing tissue 90 with the suture passer 100 at two different locations A, B within the tissue 90; (iii) advancing the free end 81 of the flexible construct 80 from one location to the other location and pulling the suture passer 100 out of the tissue 90; (iv) passing the free end 81 through an eyelet/loop 140*a* of a shuttle/pull device 140 removably attached to the soft anchor 150; (v) pulling the shuttle/pull device 140 to pass the free end 81 though the body 115 of the soft anchor 150 and form a knotless, continuous, uninterrupted, flexible, adjustable, self-locking, tensionable loop 188; and (vi) pulling the free end 81 to tension the loop 188. The method can be conducted while maintaining the soft anchor 150 outside the joint space. The free end 81 can be removably attached to a lower jaw of the suture passer 100. The steps can be repeated for additional soft anchors 150*a*, 150*b* . . . etc.

As detailed above, anchor 150 has one repair suture limb 81 (free end 81; tensioning end 81) and at least one shuttle link 140. The repair suture 81 is passed through tissue 90 (or through tissue 90 and graft 91 overlaying the tissue 90), and then shuttled through the anchor 150. The steps can be repeated multiple times if additional links are present. The steps can be repeated multiple times if additional anchors are necessary.

The suture repair detailed above attaches a graft to soft tissue by keeping the anchors outside the joint space. Suture can pass under the tissue and then can be secured to the tubular sheaths of soft anchors on top of the tissue. The suture can include one or more barbs to allow the anchors to secure to the tissue without the need to tie any knots. By placing the anchors outside the joint space, the graft can be secured in a quick, easy and safe way.

As detailed above, the suture is loaded onto a suture passer. The distal end of the suture passer is inserted through a cannula into the tissue and graft (or into tissue). The needle is then fired to transfer the suture from one tine to the other. The needle is retracted back leaving the suture in the longer tine. The device is pulled out of tissue together with the suture. The end of the suture is then passed through the sheath of the soft anchor (or sheaths of multiple soft anchors). The end is pulled to slide the anchors towards the tissue. The suture is pulled until each anchor is snug against the graft (or tissue). The barbed suture pulls one way through the anchor, preventing the construct from loosening. The excess suture is trimmed. The final construct leaves one or more self-locking anchors on top of the graft (or top of the tissue) and a horizontal mattress stitch on bottom of the tissue.

Instrument 100 with fixation device 150 pre-loaded with construct 80 can be employed in endoscopic surgery. The term "endoscopic surgery" refers to surgical procedures within a patient's body through small openings as opposed to conventional open surgery through large incisions.

The term "high strength suture" is defined as any elongated flexible member, the choice of material and size being dependent upon the particular application. For the purposes of illustration and without limitation. the term "suture" as used herein may be a cable. filament, thread, wire, fabric. or any other flexible member suitable for tissue fixation in the body.

What is claimed is:

1. A method of suturing comprising:
   fixedly attaching a first end of a flexible construct to a fixation device;

removably attaching a second end of the flexible construct to a suture passer;

inserting the suture passer and the second end of the flexible construct into a joint space while the fixation device is maintained outside the joint space;

advancing the second end of the flexible construct through tissue to be sutured so that the second end enters and exits the tissue at two separate locations;

pulling the suture passer out of the tissue;

passing the second end of the flexible construct through a body of the fixation device maintained outside of the joint space to form a tensionable loop around and through the tissue, wherein the fixation device is a soft-body fixation device; and securing the fixation device over the tissue.

2. The method of claim 1, wherein all steps are conducted while the fixation device is maintained outside the joint space.

3. The method of claim 1, wherein the soft-body fixation device consists essentially of suture.

4. The method of claim 1, wherein the flexible construct is fixedly attached to the fixation device by a loop or a knot.

5. The method of claim 1, wherein a shuttle/pull device extends through the body of the soft-body fixation device.

6. The method of claim 5, wherein the step of passing the second end of the flexible construct through the body of the fixation device further comprises:

passing the second end of the flexible construct through a closed eyelet of the shuttle/pull device; and pulling the shuttle/pull device to allow the second end of the flexible construct to form the tensionable loop, wherein the tensionable loop is a knotless, continuous, uninterrupted, flexible, adjustable, self-locking loop.

7. The method of claim 1, wherein the tissue is soft tissue, or soft tissue and graft.

8. The method of claim 1, further comprising:

pulling the second end to tension the tensionable loop around and through the tissue; and passing the second end through another body of another fixation device to form another tensionable loop around and through the tissue.

9. The method of claim 8, wherein the another fixation device is a soft-body fixation device consisting essentially of suture.

10. The method of claim 1, wherein the first end of the flexible construct is provided with a locking structure disposed on at least a portion of the first end.

11. The method of claim 10, wherein the locking structure includes one or more barbs for engaging a tubular sheath of the fixation device.

12. The method of claim 10, wherein the locking structure includes a plurality of spikes or barbs that angle outwardly in a direction toward the body of the fixation device to form a one-way lock with the fixation device.

13. A method of suturing comprising:

securing a first end of a flexible construct to a soft-body fixation device;

removably attaching a second end of the flexible construct to a suture passer;

advancing the suture passer and the second end of the flexible construct into a joint space and through tissue to be sutured so that the second end enters and exits the tissue at two separate locations, while the soft-body fixation device with the first end are maintained outside the joint space;

pulling the suture passer with the second end of the flexible construct out of the tissue;

passing the second end of the flexible construct through a body of the soft-body fixation device to form a knotless, adjustable, self-locking, tensionable loop around and through the tissue; and forming a mattress stitch connected to the soft-body fixation device, wherein the mattress stitch is located on one side of the tissue to be sutured, and the soft-body fixation device is located on and abuts another side of the tissue to be sutured, wherein all steps are conducted while the soft-body fixation device is maintained outside the joint space.

14. The method of claim 13, wherein the first end of the flexible construct is provided with a locking mechanism to lock the knotless, adjustable, self-locking, tensionable loop and prevent loosening.

15. The method of claim 14, wherein the step of forming a mattress stitch further comprises passing the second end of the flexible construct through another body of another soft-body fixation device to form another knotless, adjustable, self-locking, tensionable loop around and through the tissue.

16. The method of claim 13, wherein the step of forming a mattress stitch further comprises passing the second end of the flexible construct through multiple soft-body fixation devices to form multiple knotless, adjustable, self-locking, tensionable loop around and through the tissue.

* * * * *